United States Patent [19]

Schroeder et al.

[11] 4,436,844
[45] Mar. 13, 1984

[54] PROCESS FOR THE MANUFACTURE OF A FOUNDRY CORE OR MOULD

[75] Inventors: Arnold Schroeder, Deventer; Lodewijk Roskott, Gorssel, both of Netherlands

[73] Assignee: Akzona Incorporated, Asheville, N.C.

[21] Appl. No.: 451,638

[22] Filed: Dec. 20, 1982

[30] Foreign Application Priority Data

Dec. 21, 1981 [NL] Netherlands ........................ 8105743

[51] Int. Cl.³ .............................................. C08K 3/36
[52] U.S. Cl. ..................................... 523/144; 523/146
[58] Field of Search ........................ 823/144, 145, 146

[56] References Cited

U.S. PATENT DOCUMENTS 4,176,114 11/1979 Stewart et al. ...................... 523/144

Primary Examiner—Lewis T. Jacobs
Attorney, Agent, or Firm—Francis W. Young; Robert F. Green

[57] ABSTRACT

There is disclosed an improved process for the manufacture of a foundry core or mould, comprising forming into the foundry core or mould a composition comprising a granular filler, a synthetic resin which cures under the action of an acid and a desensitized ketone peroxide composition and treating said formed composition with sulphur dioxide, wherein the improvement comprises using as the desensitizing agent a dialkyl ester of an aliphatic dicarboxylic acid of the general formula

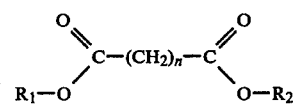

wherein n=1–7 and $R_1$ and $R_2$=a branched or non-branched alkyl group having 3 to 5 carbon atoms.

5 Claims, No Drawings

PROCESS FOR THE MANUFACTURE OF A FOUNDRY CORE OR MOULD

BACKGROUND OF THE INVENTION

The present invention relates to a process for the manufacture of a foundry core or mould, in which process a composition comprising a granular filler, a synthetic resin which cures under the action of an acid, and a desensitized ketone peroxide composition is formed into the desired foundry core or mould and treated with sulphur dioxide.

A process of the type indicated above is known from U.S. Pat. No. 3,879,339. Such a process is based on the principle of sulphuric acid being formed in situ in the composition, causing a very rapid curing of the resin, the sulphur dioxide being converted into sulphuric acid in the presence of an oxidizing agent and mere traces of water. Essential in such process is that in such a way there will be no intermediate formation of sulphur dioxide, the curing action of which is unduly violent and unselective.

The above-mentioned process is used on a large scale. A ketone peroxide generally is used, as the oxidizing agent, more particularly the methyl ethyl ketone peroxide mentioned in Example 1 of U.S. Pat. No. 3,879,339.

The transport and storage of ketone peroxides in their pure state is forbidden by law in view of the risk of decomposition and the ensuing explosion hazards. Such a drawback is generally met by incorporating the ketone peroxide into a desensitizing agent. Provided that a proper desensitizing agent is chosen, there will no longer be any premature or undesirable decomposition of the ketone peroxide, or only to such a small degree that in actual practice it does not present any real danger.

The most commonly used desensitizing agents are the dialkyl esters of phthalic acid, more particularly dimethyl phthalate and diisobutyl phthalate. However, the use in the present process of ketone peroxide compositions desensitized with those agents would lead to serious problems. For, in the manufacture of castings, the foundry cores and moulds are exposed to a temperature in the range of 700° to 1200° C. At such high temperatures the phthalic esters will decompose, attended with the production of smoke, which not only obstructs visibility in the foundry, but also irritates the mucous membranes and the eyes of the people that are present there.

The present invention not only has for its object to find a suitable desensitizing agent for ketone peroxides as will not cause the formation of bothersome decomposition products during the use of foundry cores and moulds, but also to find a ketone peroxide composition resulting in good curing of the foundry cores and moulds.

SUMMARY OF THE INVENTION

The present invention provides a solution to the aforementioned problem and is characterized in that the ketone peroxide composition contains as the desensitizing agent a dialkyl ester of an aliphatic dicarboxylic acid of the general formula:

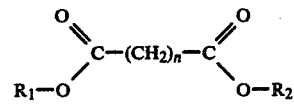

wherein $n=1-7$ and $R_1$ and $R_2=$a branched or non-branched alkyl group having 3 to 5 carbon atoms.

DETAILED DESCRIPTION OF THE PREFERRED EMBODIMENTS

It should be added that from U.S. Pat. No. 4,220,578 it is known that in the manufacture of castings or foundry moulds a dialkyl ester of dicarboxylic acids is added to the mixture of resin and sand to be cured, preference being given to dimethyl esters. These preferred compounds, however, are unsuitable to function as a desensitizing agent for ketone peroxides in that they lead to instability of the ketone peroxide.

It should also be added that British Pat. Nos. 1,095,914 and 1,256,432 and U.S. Pat. No. 3,649,546 disclose the use of dialkyl esters of aliphatic dicarboxylic acids as desensitizing agents for ketone peroxides. However, none of those patents refer to an ester of the present invention or to the possibility of using the herein described compositions in the manufacture of foundry cores or moulds.

The use of the ketone peroxide compositions of the present invention prevents the formation in the casting process of bothersome decomposition products of the desensitizing agent. It has further been found that the use of the present ketone peroxide compositions leads to a curing of the foundry cores and moulds which is equivalent or even superior to that which may be attained with the aforementioned phthalic ester compositions. Moreover, the present compositions are less viscous than the usual phthalic ester-containing compositions, which has a favorable effect on processability. Further, the present ketone peroxide compositions are found to excel as far as stability and safety are concerned.

Immediately after being gassed, the foundry core or mould is subjected to all kinds of mechanical forces. For instance, the core or mould is generally discharged from the core or mould box mechanically, placed on a conveyor belt and further transported. For the foundry cores and moulds to withstand this handling without sustaining any damage, they must be rapidly and sufficiently cured. The criterion used to that end is that 30 seconds after termination of gassing the flexural strength (in $N/cm^2$) of the foundry core or mould is at least 170 $N/cm^2$ and preferably at least 200 $N/cm^2$(=initial curing).

Sufficient final curing is, of course, of importance with a view to the forces to which the core or mould is exposed during its use. The criterion used then is that 24 hours after termination of gassing the flexural strength (in $N/cm^2$) of the core or mould is at least 270 $N/cm^2$ and preferably at least 300 $N/cm^2$. Consequently, for a foundry core or mould to be suitable for practical purposes, it must satisfy the above-mentioned requirements both as far as initial and final curing are concerned.

The composition to be used in the present process should contain a granular filler, a synthetic resin which cures under the action of an acid, and the above-mentioned ketone peroxide composition. Amongst the fillers which can be used, there may be mentioned all materials containing a high proportion of silica. Examples thereof include siliceous sand, refractory materials, metal oxides such as zirconium oxides, sillimanite and abrasive products such as carborundum and corundum. It is preferred that use should be made of siliceous sand.

All the resins that cure under the action of an acid can be used in the process according to the present invention. Numerous resins meet this criterion. Particularly suitable are the urea formaldehyde, phenol formaldehyde, furane and furane copolymer resins, which can be modified by furfuryl alcohol or by unsaturated compounds or epoxy compounds. Silanifation of these resins by γ-amino-propyl-triethoxysilane is generally desirable, but not indispensable. The proportion of resin contained in the composition will range from about 0.5 to about 10% by weight. Use may, of course, also be made of mixtures of the above-mentioned resins.

The present ketone peroxide composition may contain any ketone peroxide desired. Examples thereof include acetone peroxide, methyl ethyl ketone peroxide, diethyl ketone peroxide, methyl propyl ketone peroxide, methyl isobutyl ketone peroxide and alicyclic ketone peroxides such as cyclopentanone peroxide, cyclohexanone peroxide, methyl-cyclohexanone peroxide and trimethyl cyclohexanone peroxide. It is preferred that use should be made of methyl ethyl ketone peroxide.

The desensitizing agent into which the ketone peroxide is incorporated is of the general formula:

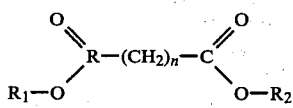

wherein n=1-7 and $R_1$ and $R_2$=a branched or nonbranched alkyl group having 3 to 5 carbon atoms.

The desensitizing agents of the present invention are prepared by esterifying the corresponding aliphatic dicarboxylic acids in a known manner. Examples of suitable esters include the esters of malonic acid, succinic acid, glutaric acid, adipic acid and pimelic acid (i.e. n=1-5). It is preferred that use should be made of esters derived from succinic acid, glutaric acid and adipic acid, and particularly mixtures of these esters. They are of importance in that mixtures of succinic acid, glutaric acid and adipic acid are obtained as waste product in the preparation of nylon 66 and are therefore readily available.

The groups $R_1$ and $R_2$ represent branched or non-branched alkyl groups having 3 to 5 carbon atoms. It is preferred that $R_1$ and $R_2$ should be the same. The ester units should not contain fewer than 3 carbon atoms, because otherwise their use according to the present process would result in insufficient initial curing. The use of ester units having more than 5 carbon atoms leads to insufficient final curing. In fact, only the use of the present esters leads to both sufficient initial and final curing of the foundry core or mould. Very good results are obtained with the use of desensitizing agents of which the ester units contain 4 carbon atoms. It is preferred that use should be made of a mixture of 10–35% by weight of diisobutyl succinate, 30–60% by weight of diisobutyl glutarate and 20–50% by weight of diisobutyl adipate.

The ketone peroxide compositions may be prepared in the usual manner by allowing the ketone to react with $H_2O_2$ under the action of $H_2SO_4$ and in the presence of the dialkyl ester. After neutralization and separation of the aqueous phase, the composition is dried. If required, some more ester may be added to the composition. Generally, the composition contains about 10 to about 75% by weight of ketone peroxide, about 10 to about 85% by weight of desensitizing agent and up to about 10% of water. For practical purposes the active oxygen content of the compositions is generally in the range of about 3 to about 11%, preferably about 6 to about 9%.

If desired, one or more usual stabilizers may be added to the composition. The desensitized ketone peroxide composition is incorporated into the composition to be cured in an amount ranging from about 0.2 to about 2% by weight, and preferably about 0.3 to about 0.7% by weight. The granular filler, the resin and the ketone peroxide composition may be intermixed in any convenient manner. The resulting mixture as such can be kept for several hours. Further, some additional agents, such as a curing accelerator, may be incorporated into the composition to be cured. Suitable for that purpose are, for example, benzene sulphonyl chloride, paratoluene sulphonic acid, benzoquinone and hydroxylamine hydrochloride. A subsequent step in the production of a mould from the composition consists of packing the mixture around a desired pattern. After manual, mechanical, hydraulic or pneumatic compacting of the composition sulphur dioxide gas is introduced into it. The injection of gas may be conducted in a manner, for instance, as described in U.S. Pat. No. 3,879,339. It will generally be carried out at room temperature and at a pressure which can vary depending on the dimensions of the core or mould to be manufactured. The pressures which are usually employed are between about 0.5 and about 5 atmospheres.

Following the injection of sulphur dioxide the composition is generally flushed with a neutral gas such as air in order to expel any sulphur dioxide left. The treatment with sulphur dioxide and air takes about 10 to 20 seconds in all. Subsequently, the mould or core is removed from the mould box or core box and carried off. The resulting foundry cores and moulds satisfy all requirements to be met for their use in the manufacture of castings. The present process may be applied in a simple manner and at high speed in the metal foundry industry.

It should be added that the present ketone peroxide compositions also may be used for purposes other than that described hereinbefore, for instance, for curing unsaturated polyester resins, acrylic esters, and methacrylic esters. The present invention will be further described in the following nonlimiting examples.

EXAMPLE 1

A great many methyl ethyl ketone peroxide compositions desensitized with the compounds mentioned in Table 1 were prepared as follows.

Into a 500 ml three-necked flask there were charged, with stirring, 110 grams of dialkyl ester, 44.3 grams of methyl ethyl ketone and 1.8 grams of 4 N—$H_2SO_4$. Subsequently, 51.4 grams of a 70%—$H_2O_2$ solution were added over a period of about 30 minutes. The temperature was maintained at 28° to 32° C. with the aid of ice water. After stirring for 1 more hour at 30° C. the composition was neutralized to a pH of 5.5 to 6.5 by adding a 4 N-sodium hydroxide solution. After separation of the aqueous and the organic phase, the latter phase was dried in vacuo in a rotating vacuum evaporator. If still necessary, the active oxygen content was set to 7.0% by adding dialkyl ester.

EXAMPLE 2

All the methyl ethyl ketone peroxide compositions prepared according to Example 1 were used in the formation of a foundry core measuring 2.2×2.2×17 cm. In a core sand mixer of the PKM type (supplied by George Fisher) 3000 parts of sand (55 AFA, supplied by Sigrano) and a mixture of 30 parts of furan resin (Hardox 80, supplied by Sapic) and 0.09 parts of γ-aminopropyl triethoxysilane (Silane A1100, supplied by Union Carbide) were intermixed over a period of 2 minutes. Subsequently, 15 parts of the methyl ethyl ketone peroxide composition were added, followed by mixing for another 1.5 minutes. Next, the composition was placed in a core box, compacted, and the excess sand mixture scraped off. In a following step the core box was placed in a gassing apparatus by which, at room temperature and for 1 second, $SO_2$ was forced through it at a pressure of 2.5-3 bar. Following this operation the core was flushed with air at a pressure of about 1.5 bar, after which the core was removed from the box. The flexural strength of the core was measured 30 seconds and 24 hours after termination of the gassing operation in the manner described in DIN 52404. The results are listed in Table 1.

EXAMPLE 3

As in Example 1, there were charged into a three-necked flask 60.0 g of diisobutyl nylonate, 98.0 g of methyl isobutyl ketone and 26.0 g of 50%—$H_2SO_4$. Subsequently, 95.5 g of a 70%—$H_2SO_4$ solution was added over a period of 30 minutes, with the reaction mixture being kept at 20°-22° C., followed by 2 hours stirring. The pH was brought to a value of 5.5-6.6 with the aid of sodium hydroxide and after drying in vacuo the active oxygen content was set to 7% by adding diisobutyl nylonate.

EXAMPLE 4

As in Example 1, there were charged into a three-necked flask 70.75 g of 70%—$H_2O_2$, 72.5 g of diisobutyl nylonate and 0.565 ml of 2 N—$H_2SO_4$. Subsequently, 28.0 g of cyclohexane were added over a period of 60 minutes at a temperature of 20°-22° C., after which stirring was continued for 1 hour. This was followed by neutralization with 4 N-sodium hydroxide, separation and drying the peroxide under reduced pressure. The active oxygen content was set to 7% by adding diisobutyl nylonate.

EXAMPLE 5

The methyl isobutyl ketone peroxide as prepared in

TABLE 1

| DESENSITIZING AGENT WITHIN INVENTION | FLEXURAL STRENGTH OF CORE IN N/cm² | | DESENSITIZING AGENT OUTSIDE INVENTION | FLEXURAL STRENGTH OF CORE IN N/cm² | |
|---|---|---|---|---|---|
| | AFTER 30 SECONDS | AFTER 24 HOURS | | AFTER 30 SECONDS | AFTER 24 HOURS |
| | | | dimethyl phthalate | 75 | 330 |
| | | | diisobutyl phthalate | 200 | 345 |
| dibutyl malonate | 195 | 400 | diethyl malonate | 155 | 385 |
| | | | di(2-ethylhexyl) malonate | 170 | 270 |
| | | | dimethyl malonate | 105 | 175 |
| di-n.pentyl succinate | 205 | 340 | dimethyl succinate | 55 | 255 |
| | | | diethyl succinate | 105 | 400 |
| diisopropyl adipate | 175 | 430 | dimethyl adipate | 75 | 365 |
| di-n.propyl adipate | 190 | 390 | diethyl adipate | 160 | 445 |
| diisobutyl adipate | 215 | 310 | di(2-ethylbutyl) adipate | 170 | 235 |
| di-sec.butyl adipate | 210 | 370 | di-n-hexyl adipate | 175 | 225 |
| di-n.butyl adipate | 215 | 350 | di-n-heptyl adipate | 175 | 225 |
| di-n.pentyl adipate | 200 | 300 | di(2-ethylhexyl) adipate | 170 | 205 |
| diisopentyl adipate | 185 | 275 | | | |
| di-sec.pentyl adipate | 210 | 375 | | | |
| di-neopentyl adipate | 180 | 275 | | | |
| di-n.propyl azelainate | 215 | 330 | di(2-ethylhexyl)azelainate | 165 | 205 |
| diisobutyl azelainate | 185 | 290 | dimethyl azelainate | 90 | 480 |
| di-n.butylazelainate | 180 | 290 | | | |
| diisobutyl nylonate* | 210 | 385 | dimethyl nylonate* | 70 | 295 |
| | | | di(2-ethylhexyl) nylonate* | 175 | 225 |
| di-n.propyl suberate | 215 | 335 | | | |
| diisopentyl glutarate | 175 | 350 | dimethyl glutarate | 75 | 320 |
| di-n.butyl glutarate | 210 | 340 | | | |
| diisobutyl pimelate | 215 | 330 | | | |
| di-n.pentyl pimelate | 180 | 275 | | | |
| | | | diisopentyl sebacate | 175 | 220 |
| | | | di(2-ethylhexyl) sebacate | 160 | 200 |
| | | | diisopentyl dodecanedioate | 175 | 215 |

*nylonate is a mixture of 20% by weight of succinate, 45% by weight of glutarate and 35% by weight of adipate.

Table 1 shows that the use of the present esters leads to results that are equivalent to or better than those obtained with the use of the known phthalic esters. It is also clear that the use of the present dialkyl esters leads to a better curing than the use of dialkyl esters of aliphatic dicarboxylic acids which do not satisfy the aforementioned general formula. Finally, it appears that the best results are obtained by using branched or non-branched butyl esters.

accordance with Example 3 and the cyclohexanone peroxide as prepared in accordance with Example 4 were used in the formation of foundry cores. The results are given in Table 2.

TABLE 2

| PEROXIDE AND DESENSITIZING AGENT | FLEXURAL STRENGTH OF CORE IN N/cm² | |
|---|---|---|
| | after 30 seconds | after 24 hours |
| methyl isobutyl ketone peroxide in diisobutyl nylonate | 210 | 370 |
| cyclohexanone peroxide in diisobutyl nylonate | 185 | 390 |

What is claimed is:

1. An improved process for the manufacture of a foundry core or mould, comprising forming into the foundry core or mould a composition comprising a granular filler, a synthetic resin which cures under the action of an acid and and a desensitized ketone peroxide composition and treating said formed composition with sulphur dioxide, wherein the improvement comprises using as the desensitizing agent a dialkyl ester of an aliphatic dicarboxylic acid of the general formula

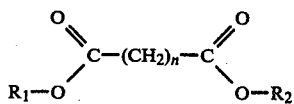

wherein $n = 1-7$ and $R_1$ and $R_2 =$ a branched or non-branched alkyl group having 3 to 5 carbon atoms.

2. The process of claim 1 wherein $R_1$ and $R_2$ represent a branched or non-branched butyl group.

3. The process of claim 1 wherein n is equal to 2, 3 or 4.

4. The process of claim 1 wherein the ketone peroxide composition comprises a mixture of diisobutyl succinate, diisobutyl glutarate and diisobutyl adipate.

5. The process of claim 1 wherein the ketone peroxide is methyl ethyl ketone peroxide.

* * * * *